United States Patent [19]

Canning et al.

[11] Patent Number: 4,789,736

[45] Date of Patent: Dec. 6, 1988

[54] COMPLEXES OF TECHNETIUM-99M WITH PROPYLENE AMINE OXIMES

[75] Inventors: Lewis R. Canning, Herts; David P. Nowotnik; Rudi D. Neirinckx, both of Bucks; Ian M. Piper, Herts, all of England

[73] Assignee: Amersham International plc, Bucks, England

[21] Appl. No.: 838,558

[22] Filed: Mar. 11, 1986

[30] Foreign Application Priority Data

Mar. 11, 1985 [GB] United Kingdom ............... 8506249
Apr. 12, 1985 [GB] United Kingdom ............... 8509368

[51] Int. Cl.$^4$ ................. C07C 131/14; C07C 131/08; C07F 17/00; A61K 49/02
[52] U.S. Cl. .................................... 534/14; 424/1.1; 564/253; 564/268
[58] Field of Search ............ 424/1.1; 534/14; 564/253, 268

[56] References Cited

U.S. PATENT DOCUMENTS 4,615,876 10/1986 Troutner et al. ............... 534/14 X

FOREIGN PATENT DOCUMENTS 0123504 10/1984 European Pat. Off. ............. 534/14

OTHER PUBLICATIONS

Smith, D. F., CRC Handbook of Stereoisomers: Drugs in Psychopharmacology, ed. D. F. Smith, CRC, Boca Raton, Fla. 1984, p. 11.

Primary Examiner—John F. Terapane
Assistant Examiner—Virginia B. Caress
Attorney, Agent, or Firm—Wenderoth, Lind & Ponack

[57] ABSTRACT

A family of propylene amine oxime ligands has the formula 2

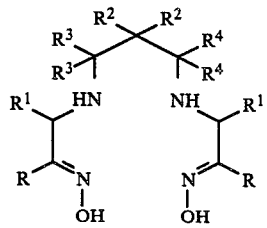

wherein preferably $R^1$ is Cl-C4 alkyl or phenyl and each of R, $R^2$, $R^3$ and $R^4$ is H or Cl-C4 alkyl. The technetium-99m complexes of these ligands are lipophilic neutral complexes useful as diagnostic radiopharmaceuticals and particularly for brain scanning. The ligands show stereoisomerism. The preparation and properties of the dl- and meso-stereoisomers, and of the d- and l-enantiomers, are described. The l-enantiomer and the dl-stereoisomer of the preferred compound (2, $R=R^1=R^2=CH_3$, $R^3=R^4=H$) show good retention in the brain.

9 Claims, No Drawings

COMPLEXES OF TECHNETIUM-99M WITH PROPYLENE AMINE OXIMES

Technetium-99m (Tc-99m) is the favoured radionuclide for organ imaging and other forms of in vivo diagnosis. Complexes of Tc-99m have been used for investigating most parts of the body.

This invention relates to complexes of Technetium-99m useful as diagnostic pharmaceuticals, and in particular to complexes which are capable of crossing the blood-brain barrier and being retained in the brain for a time to permit diagnosis.

European Patent Specification 123504 provides a lipophilic macrocyclic complex of Technetium-99m useful as a diagnostic radiopharmaceutical which can be formed by complexing in aqueous solution Tc-99m pertechnetate under reducing conditions with an alkylene amine oxime containing 2 or 3 carbon atoms in the alkylene group, which group is unsubstituted or substituted, the complex having a core with a zero net charge, containing an O—H—O ring closure bond, and being sufficiently stable for parenteral administration and imaging by scintilation scanning, any alkylene subsituents present being of the kind useful for adapting radionuclide ligands for body imaging applications. Preferred complexes are believed to have the formula:

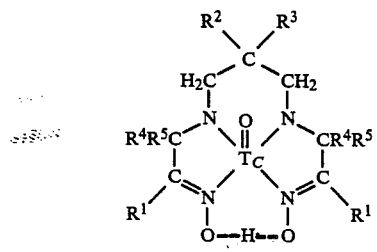

where each $R^1$, $R^4$, and $R^5$ is hydrogen or C1 to C12 alkyl, and each of $R^2$ and $R^3$ is hydrogen, hydroxyl, C1 to C12 alkoxyl, C1 to C22 hydrocarbon which may be alkyl, alkenyl, alkaryl, aralkyl or aryl, or tertiary amine with 1 to 20 carbon atoms, or $R^2$ and $R^3$ form, together with the carbon atom to which they are attached, a cycloaliphatic group which may be amine substituted.

The present invention relates to a family of complexes, and the associated ligands, falling within the scope of the invention of the aforesaid European patent specification but not specifically described therein, which complexes show interesting properties particularly as regards brain retention. An important member of the family is a lipophilic macrocyclic complex, useful as a diagnostic radiopharmaceutical, of Technetium-99m with a propylene amine oxime ligand having the formula 1:

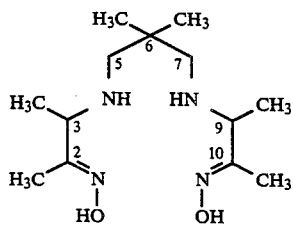

The compound of formula 1, together with some other propylene amine oximes according to the aforesaid European Patent Specification, have two asymmetric carbon atoms and thus exist in the form of three stereoisomers. Another important aspect of this invention results from the unexpected discovery that there are significant differences between the in vivo properties of Tc-99m complexes of these stereoisomers.

The present invention provides a lipophilic macrocyclic complex, useful as a diagnostic radiopharmaceutical, of Technetium-99m with a propylene amine oxime ligand having the formula 2:

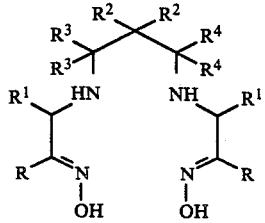

where R is H, alkyl, aryl, cycloalkyl, $CF_3$, $CONX_2$ or $C_6H_4OCH_3$.

R is alkyl, aryl, cycloalkyl or $CF_3$, or R and $R^1$ together form part of a cycloalkyl ring, each of $R^2$, $R^3$ and $R^4$ is H, alkyl, aryl, cycloalkyl or $CF_3$, and X is H, $CH_3$, $C_2H_5$ or $C_6H_5$, wherein the ligand of formula 2 is in the form of a single stereoisomer or of a mixture of 2 or more such stereoisomers, provided that, where R is methyl and $R^1$ is methyl and $R^2$, $R^3$ and $R^4$ are hydrogen, a mixture of 3 such stereoisomers contains an artificially high concentration of one of them.

The ligands of general formula 2. include a pair of groups R, a pair of groups $R^1$, a pair of groups $R^2$, a pair of groups $R^3$ and a pair of groups $R^4$, five pairs in all. The two groups constituting each pair may be the same or different. When they are the same (and when $R^3$ is the same as $R^4$), as is the case with the compound of formula 1., the ligands exist in the form of three stereoisomers, by virtue of the two asymmetric carbon atoms to which the groups $R^1$ are attached. When the two groups constituting one or more of the five pairs are different from one another (or when $R^3$ is different from $R^4$), the stereochemistry becomes more complex. For simplicity hereafter, the two groups constituting each of the five pairs will be treated as being the same. But it should be understood that the invention is not so limited.

There follows, by way of example, a list of compounds which are propylene amine oxime ligands of formula 2 in which the two groups constituting each pair are the same (except in the case of compound 11 where the $R_2$'s are different; and compound 12 wherein both the $R_3$'s and the $R_4$'s are different):

| Compound | R | $R^1$ | $R^2$ | $R^3, R^4$ |
|---|---|---|---|---|
| 1 | $CH_3$ | $CH_3$ | $CH_3$ | H |
| 2 | $CH_3$ | $CH_3$ | H | H |
| 3 | $CH_3$ | $C_2H_5$ | H | H |
| 4 | $C_2H_5$ | $CH_3$ | H | H |
| 5 | n-$C_3H_7$ | $CH_3$ | H | H |
| 6 | $C_2H_5$ | $CH_3$ | $CH_3$ | H |
| 7 | $CH_3$ | $CH_3$ | $C_2H_5$ | H |
| 8 | n-$C_3H_7$ | $CH_3$ | $CH_3$ | H |
| 9 | H | $CH_3$ | H | H |

-continued

| Compound | R | $R^1$ | $R^2$ | $R^3,R^4$ |
|---|---|---|---|---|
| 10 | $CH_3$ | Ph | H | H |
| 11 | $CH_3$ | $CH_3$ | $H,CH_3$ | H |
| 12 | $CH_3$ | $CH_3$ | H | $CH_3,H$ |
| 13 | $i-C_3H_7$ | $CH_3$ | H | H |

Compound 2 is mentioned in European Patent Specification 123504. The remaining compounds and their Tc-99m complexes are believed new. Additionally, single stereoisomers, and mixtures of two or more such stereoisomers including an artificially high concentration of one of them, of all the compounds (including compound 2), and their Tc-99m complexes are believed new. All the compounds are capable of forming complexes with radioactive and non-radioactive isotopes of metals other than technetium, for example, palladium and platinum, which complexes may have useful properties for therapy and diagnosis. The following diagram shows how compound 1, by way of example, exists in the form of an optically inactive meso-diastereoisomer and of optically active d- and l-enantiomers.

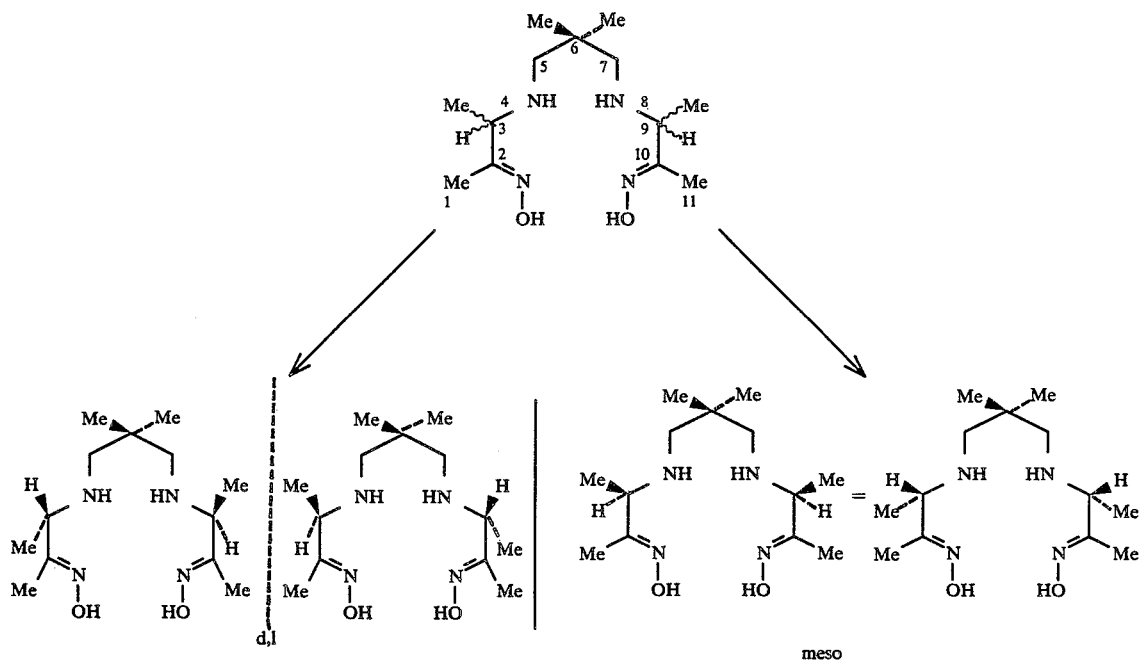

Diastereoisomers of Compound 1

The isomerism arises because the 3- and 9-carbon atoms are asymmetric. The meso-diastereoisomer has distinctly different properties from the dl-diastereoisomer (a racemic mixture of the d- and l-enantiomers). For exampole, they have different melting points, and their retention times on HPLC systems can also differ. The Tc-99m complexes from the two diastereoisomers have markedly different in vivo properties (% i.d. taken up in brain of rats). From these observations, it is to be expected that similar differences will occur in other compounds of formula 2 shown above; i.e. the two diastereoisomers derived from any one compound will have different physical properties, and the Tc-99m complexes derived from the two diastereoisomers (from a single compound) will display differences in in vivo distribution.

It has further been determined that the d- and l-enantiomers of compound 1 have properties (physical and biological) which differ from each other, and from a racemic mixture of the two enantiomers, and from the meso-diastereoisomer. Again, it is to be expected that similar differences will occur in other compounds of formula 2 shown above.

The different in vivo properties of Tc-99m complexes of the two diastereoisomers is surprising. These complexes are thought to cross the blood-brain barrier by a passive diffusion mechanism. The ability of molecules to diffuse through membranes is related in a positive way to lipophilicity and in a negative way to molecular weight. On this basis only relatively small differences in the amount of radioactivity in the brain would be anticipated since the molecular weights of the two isomers are identical and the lipophilicities of the Tc-99m complexes are thought to be very similar. Consequently the magnitude of the difference in brain uptake of the two isomers is surprising—a factor of 2.3 is involved in the case of compound 1. The better of the two isomers is the dl-isomer.

Similarly, there is a surprising difference in brain uptake of the d- and l-enantiomers of compound 1—a factor of 1.6 has been found in studies with rats.

Each of the three stereoisomers so far mentioned can itself exist in three different isomeric forms by virtue of the restricted rotation about their C=N bonds of the two oxime groups. The isomers may have different physical properties (m.p., b.p.) and can be separated by chromatographic techniques (TLC and HPLC). Their interconversion is generally facile and is catalysed by mineral or Lewis acids, bases or metal ions.

Compound 1 has two oxime groups so 3 isomers are possible:

EE

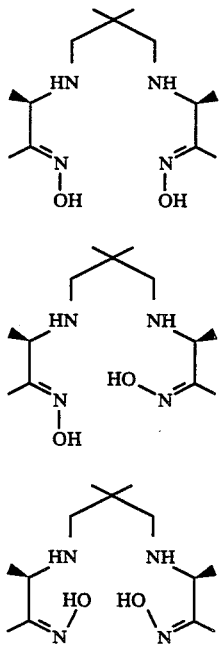

EZ

ZZ

Note that EZ is identical to ZE. The same considerations apply to both 'd' and 'l' isomers, i.e. each has three (EE, ZZ and EZ) oxime isomers. The thermodynamically preferred isomer is expected to be EE since that has the maximum separation of the bulkier groups. HPLC analysis of compound 1 (Example 11A) displays two major peaks, identified as the EE oximeisomers of the meso- and d,l-diastereoisomers, plus four minor peaks, provisionally assigned as the EZ and ZZ oxime isomers of each diastereoisomer. It is probable that the EE, EZ and ZZ isomers may form Tc-99m complexes having different biodistribution properties.

The propylene amine oxime ligands may be prepared by standard chemical routes, as generally described in the aforesaid European Patent Specification 123504. A preferred preparative route is described below in Example 1. (When the two groups R, and/or the two groups $R^1$, are different, the ligands can be prepared by an analogous route involving: reaction of a monoprotected propanediamine with one molar eqivalent of a suitable dione monoxime; reduction of the resulting imine; deprotection; reaction of the resulting primary amine with a different dione monoxime followed by reduction of the resulting second imino group.)

The compounds are generally obtained in the form of a mixture of all three isomers. The meso-isomer can be separated from the dl-mixture by standard techniques such as repeated fractional crystallisation from a solvent in which their solubilities are different; we have used acetonitrile and ethyl acetate with success. The analytical or preparative separation of the isomers can also be effected by HPLC. The d- and l-enantiomers can be separated by standard techniques involving the use of optical isomers of an organic acid such as tartaric acid. Separation techniques are detailed in Examples 14 to 20 below.

The complexation reaction between the propylene amine oxime ligand and pertechnetate ($TcO_4^-$ from generator eluate) may be carried out in aqueous or aqueous/organic solution under reducing conditions. Stannous salts are convenient reducing agents, but other reducing agents are well known for this type of reaction and can be used. Since the complexes of this invention contain Tc-99m bound rather strongly, they can alternatively be prepared by a process of ligand exchange. The preparation of Tc-99m complexes by reducing pertechnetate in the presence of a complexing ligand is well-known; the conditions for such general reactions are also well-known and can be used in the particular instance of this invention. These complexes are presently believed to have the structure 3:

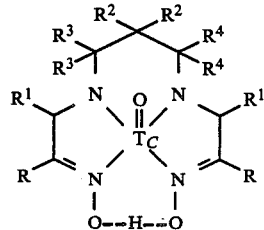

3.

The Tc-99m complex of compound 1 (an unseparated dl/meso mixture) displays:

(1) Good uptake in the brain of rats and humans.
(2) Slow removal of radioactivity from brain in humans, allowing tomographic imaging to be performed with conventional rotating gamma camera equipment.

Its advantages over the Tc-99m complex of compound 2 are:

(1) Far better in vitro stability (see Example 21 below).
(2) Better blood and tissue background clearance of activity in humans.
(3) The complex of compound 2 may not be suitable for radiopharmaceutical applications because of rapid in vitro degradation, but the complex of compound 1 is ideally suited as it displays only slow in vitro degradation. (See Example 26 below).

The complex of compound 1 (dl-isomer) is surprisingly superior to the complex of the meso-isomer, so far as brain retention and brain imaging are concerned. By contrast, the complexes of compound 2 (dl-isomer) and compound 2 (meso-isomer) do not show any marked difference in brain uptake (see Example 24 below).

The complex of compound 1 (both the unseparated dl/meso mixture and the dl-isomer) also show other interesting and unexpected properties:

They are good tumour blood flow agents (unpublished article of V. R. McCready et al submitted to Journal of Nuclear Medicine).

They are good agents for labelling blood cells, particularly leucocytes. (See Example 27 below).

The biodistribution properties of compounds 3 to 13 (see Example 22 below) also indicate various uses for these compounds as diagnostic pharmaeuticals, both in the form of their unseparated dl/meso isomer mixtures and in the form of their separated isomers.

They are useful for myocardial perfusion imaging.
The following Examples illustrate the invention.

EXAMPLE 1

Preparation of the Compound 1

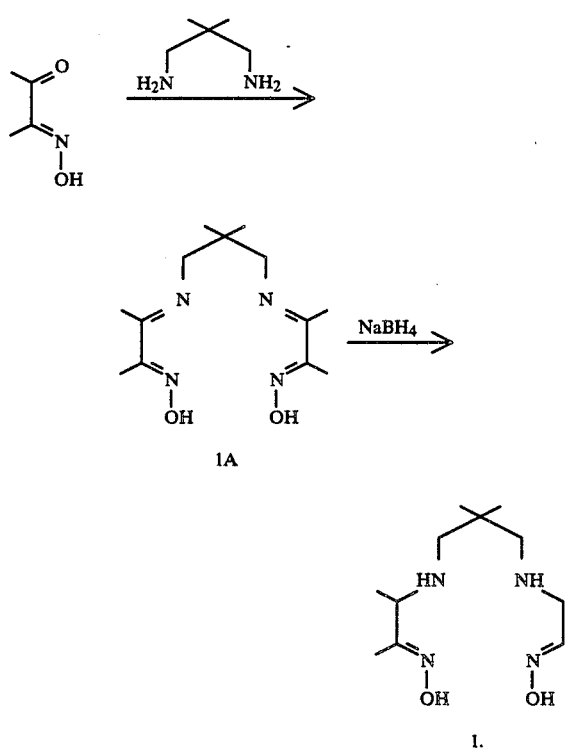

1A.
4,8-Diaza-3,6,6,9-tetramethyl-3,8-undecadiene-2,10-dione bis oxime 2,3-Butanedione monoxime (11.66 g, 115.4 mmol) was dissolved in benzene (50 cm³) containing acetic acid (75 μl), and the solution was brought to reflux in an apparatus fitted with a Dean-Stark trap and in a nitrogen atmosphere. To this was added a solution of 2,2-dimethyl-1,3-propanediamine (5.00 g, 5.88 cm³, 49 mmol) in benzene (100 cm³) over a period of 5 hours. The resulting yellow-brown solution was refluxed for a further 16 hours under nitrogen, then allowed to cool to room temperature. The resulting solid was filtered off under suction and washed with a little cold (−40° C.) acetonitrile giving the product as a fine white powder. After drying under high vacuum for 2 hours 7.9 g (60% yield) of product was obtained, m.p. 131°–134° C. The product thus obtained contains a trace (ca. 2%–5%) of starting ketooxime (as seen by ¹H NMR), but this can be removed completely by a single recrystallisation from benzene, giving a product melting at 132° C.–135° C.

NMR(¹H, 60 MHz, CDCl₃): δ3.3(4H, brs, CN₂N), 2.1(6H, s, CH₃—C=N), 2.0 (6H, s, CH₃—C=N) 1.1(6H, s, (CH₃)₂C)ppm.

1. 4,8-diaza-3,6,6,9-tetramethylundecane-2,10-dione bis oxime

The diimine (75 g, 287 mmol) was slurried in 95% aqueous ethanol (690 cm³) at 0° C. Sodium borohydride (10.9 g, 287 mmol) was added in portions over ½ hour and the mixture stirred at 0° C. for 2 hours. Water (230 cm³) was added and the mixture stirred well for a further 2 hours. The ethanol was removed in vacuo and more water (140 cm³) added. The pH was adjusted to around 11 then the resulting white solid was filtered, washed with a little water and dried in vacuo giving the crude product. Double recrystallisation from hot acetonitrile gave pure product 62.5 g, (80%) m.p. 144° C.–145° C.

NMR (¹H, 200 MHz, DMSO): δ10.24(2H, s, OH) 3.13(2H, q, CHMe), 2.12(14, m, CH₂N), 1.65(6H, s, MeC=N), 1.07(6H, d, CHMe), 0.78(6H, s, CMe₂)ppm.

EXAMPLES 2 TO 13

Preparation of 2,3-pentanedione-3-oxime

Methyl nitrite was bubbled, at a rate sufficient to maintain vigorous reflux, into a well-stirred mixture of 2-pentanone (102 g) ether (400 cm³) and concentrated hydrochloric acid (15 cm³). The methyl nitrite gas was generated by the dropwise addition of a mixture of concentrated sulphuric acid (100 cm³) and water (95 cm³) onto a stirred slurry of sodium nitrite (112 g), methanol (66 g) and water (75 cm³). After the addition was complete the mixture was neutralised with saturated aqueous sodium bicarbonate (32 g in 300 cm³). The ether layer was separated and the aqueous layer extracted with more ether. The combined organic layers were dried and concentrated in vacuo giving a yellow oil which crystallised on standing. Recrystallisation from hot hexane gave pure product (67 g), m.p. 54°–5° C.

The following were prepared in a similar manner (yield and melting point given):
2,3-Pentanedione-2-oxime (46%, mp 59°–61° C.)
2,3-Hexanedione-3-oxime (64%, mp 42°–3° C.)
1,2-Propanedione-1-oxime (18% mp 61°–5° C.)
2-methyl-3,4-pentanedione-3-oxime (45% m.p. 72°–75° C.).

Preparation of Compounds 2A to 13A

The following diimines were prepared in a similar manner to Example 1 (yields and melting points given):
4,8-Diaza-3,9-dimethyl-3,8-undecadiene-2,10-dione bis oxime (2A), (51%, m.p. 91°–2° C.).
4,8-Diaza-3,9-diethyl-3,8-undecadiene-2,10-dione bis oxime (3A), (68%, m.p. 76°–8° C.).
5,9-Diaza-4,10-dimethyl-4,9-tridecadiene-3,11-dione bis oxime (4A), (31%, m.p. 143.5°–144.5° C.).
6,10-Diaza-5,11-dimethyl-5,10-pentadecadiene-4,12-dione bis oxime (5A), (30%, m.p. 130°–1° C.
5,9-Diaza-4,7,7,10-tetramethyl-4,9-tridecadiene-3,11-dione bis oxime (6A) (49%, m.p. 79°–82° C.).
4,8-Diaza-6,6-diethyl-3,9-dimethyl-3,8-undecadiene-2,10-dione bis oxime (7A) (67%, m.p. 168°–9° C.).
6,10-Diaza-5,8,8,11-tetramethyl-5,10-pentadecadiene-4,12-dione bis oxime (8A) (32% m.p. 91°–3° C.).
3,7-Diaza-2,8-dimethyl-2,7-nonadiene-1,9-dione bis oxime (9A) (87%, m.p. 124° C., dec)
4,8-Diaza-3,9-diphenyl-3,8-undecadiene-2,10-dione bis oxime (10A) (59%, m.p. 169°–172° C.).
4,8-Diaza-3,6,9-trimethyl-3,8-undecadiene-2,10-dione bis oxime (11A), (70%, oil).
4,8-Diaza-3,5,7,9-tetramethyl-3,8-undecadiene-2,10-dione bis oxime (12A), (98%, oil).
5,9-Diaza-2,4,10,12-tetramethyl-4,9-tridecadiene-3,11-dione bis oxime (13A), (27%, m.p. 120° C.).

Preparation of Compounds 2 to 13

The following ligands were prepared in a similar manner to Example 1 (yields, melting points and NMR data given):

4,8-Diaza-3,9-dimethylundecane-2,10-dione bis oxime (2), (18%, m.p. 119°–122° C.).
NMR ($^1$H, 200 MHz, d$_6$-DMSO): δ10.2(2H, s, OH), 3.2(2H, q, CH), 2.3(4H, t, CH$_2$N) 1.65(6H, s, N=CMe), 1.44(2H, m, CH$_2$), 1.04(6H, d, CH)ppm.

4,8-Diaza-3,9-diethylundecane-2,10-dione bis oxime (3), (76%, oil)
NMR($^1$H, 200 MHz, d$_6$-DMSO: δ10.28(2H, s, OH), 2.90(2H, m, CH), 2.3(4H, brm, CH$_2$N), 2.19(4H, q, CH$_2$Me), 1.61(6H, s, N=CMe), 1.4(2H, m, CH$_2$), 0.98 and 0.76(6H, t, CH$_3$)ppm.

5,9-Diaza-4,10-dimethyltridecane-3,11-dione bis oxime (4), (59%, oil).
NMR($^1$H, 200 MHz, CDCl$_3$): δ3.33(2H, q, CH), 2.61(4H, q, N=CCH$_2$), 2.18(4H, m, CH$_2$N), 1.68(2H, m, CH$_2$), 1.24 and 1.13(12H, m, CH$_2$)ppm.

6,10-Diaza-5,11-dimethylpentadecane-4,12-dione bis oxime (5), (57%, oil).
NMR($^1$H, 200 MHz, CDCl$_3$): δ3.31(2H, q, CH), 2.62(4H, m, N=CCH$_2$), 2.40(4H, m, CH$_2$N), 1.57(6H, m, CH$_2$CH$_2$). 1.23(6H, m, CHMe), 0.97(6H, t, CH$_3$)ppm.

5,9-Diaza-4,7,7,10-tetramethyltridecane-3,11-dione bis oxime (6), (33%, m.p. 120°–1° C.).
NMR($^1$H, 200 MHz, d$_6$-DMSO): δ10.2(2H, s, OH), 3.15(2H, q, CH), 2.2(8H, brm, CH$_2$N+N=CCH$_2$), 1.13(6H, d, CH$_3$), 1.05(6H, t, CH$_3$), 0.78(6H, s, CMe$_2$)ppm.

4,8-Diaza-6,6-diethyl-3,9-dimethylundecane-2,10-dione bis oxime (7), (10%, m.p. 142°–4° C.).
NMR($^1$H, 200 MHz, CDCl$_3$): δ3.36(2H, m, CH), 2.39(4H, s, CH$_2$N), 1.85(6H, s, C=NMe), 1.25(10H, m, CH$_2$Me+CHCH$_3$), 0.76(6H, m, CH$_3$)ppm.

6,10-Diaza-5,8,8,11-tetramethylpentadecane-4,12-dione bis oxime (8), (5%, m.p. 134°–5° C.).
NMR($^1$H, 200 MHz, d$_6$-DMSO): δ3.19(2H, q, CH), 2.30(4H, s, CH$_2$N), 2.25(4H, m, N=CCH$_2$), 1.49(4H, brm, CH$_2$CH$_3$), 1.13(6H, d, CHMe), 0.90(12H, m, CH$_3$)ppm.

3,7-Diaza-2,8-dimethylnonane-1,9-dione bis oxime (9), (13%, m.p. 111°–4° C.).
NMR($^1$H, 200 MHz, d$_6$-DMSO): δ10.46(2H, brs, OH), 7.05 and 6.45 (2H, d, N=CH), 3.15(2H, m, CH), 2.44 (4H, brm, CH$_2$N), 1.47(2H, m, CH$_2$CH$_2$), 1.07(6H, d, Me)ppm.

4,8-Diaza-3,9-diphenylundecane-2,10-dione bis oxime (10), (22%, m.p. 101°–5° C.).
NMR($^1$H, 200 MHz, d$_6$-DMSO): δ10.50(2H, brs, OH), 7.3(10H, m, Ph), 4.29(2H, s, CHPh), 2.48(4H, m, CH$_2$N), 1.63(2H, brm, CH$_2$CH$_2$), 1.54(6H, s, CH$_3$)ppm.

4,8-Diaza-3,6,9-trimethylundecane-2,10-dione bis oxime (11), (40% oil).
NMR ($^1$H, 200 MHz, d$_6$-DMSO): δ3.3 (2H, q, CH) 2.4 (4H, m, CH$_2$), 1.8 (6H, s, CH$_3$), 1.16 (6H, d, CH$_3$), 0.7–1.4 (1H, m, CH), 0.85 (3H, d, CH$_3$)$_{ppm}$.

4,8-Diaza-3,5,7,9-tetramethylundecane-2,10 bis oxime (12), (5%, m.p. 138°–145° C.).
NMR ($^1$H, 200 MHz, d$_6$-DMSO) δ2.5 (2H, m, CH), 1.65 (6H, s, CH$_3$), 1.23 (2H, t, CH$_3$), 1.01 (6H, d, CH$_3$), 0.85 (6H, m, CH$_3$) ppm.

5,9-Diaza-2,4,10,12-tetramethyltridecane-3,11-dione bis oxime (13), (5.4%, m.p. 127°–128° C.).

NMR ($^1$H, 200 MHz, CDCl$_3$) δ3.4–3.6 (2H, q, CH), 2.5–2.8 (4H, m, CH$_2$), 2.3–2.5 (2H, m, CH), 1.6–1.8 (2H, m, CH$_2$), 1.6–1.8 (2H, m, CH$_2$), 1.4 (6H, d, CH$_3$), 1.15 (12H, d, CH$_3$) ppm.

EXAMPLE 14

Separation of meso- and d,l-stereoisomers of Compound 1

A. HPLC.

The analytical separation of the meso- and d,l-diastereoisomers was accomplished by normal-phase HPLC using a 250×4.6 mm stainless steel column packed with 5 μm silica gel microspheres connected to a commercial dual pump chromatographic system. Detection was via a variable UV detector set at 210 nm, and output from the detector was directed to a chart recorder and microcomputer programmed for peak integration.

The solvent system used throughout consisted of a mixture of 85% methanol and 15% 0.4M aqueous ammonia (v/v). In order to exclude the possibility of column degradation using this solvent system, a precolumn packed with silica gel 15 μm–25 μm particles was placed in the solvent line before the sample injector. The flow rate used throughout was 1 ml min$^{-1}$.

Samples consisting of a mixture of diastereoisomers of Compound 1 were dissolved in methanol at a concentration of 10 mg ml$^{-1}$, and 10 μl aliquots were analysed. Baseline resolution was obtained with no evidence of tailing, and retention times of 8.90 min and 9.87 min were recorded for the meso-E,E- and d,l-E,E-isomers respectively.

B. Fractional Crystallisation meso-4,8-Diaza-3,6,6,9-tetramethylundecane-2,10-dione bis oxime A sample of crude product, obtained direct from the aqueous work up (38 g, ratio 60:40, meso:dl) was recrystallised four times successively from hot acetonitrile giving pure meso isomer as fine white needles (10.5 g), m.p. 149.5°–150° C.

dl-4,8-Diaza-3,6,6,9-tetramethylundecane-2,10-dione bis oxime

A sample of crude product (9.8 g, ratio 50:50) was doubly recrystallised from hot acetonitrile giving dl-enriched material (4.6 g, ratio 47:53 meso:dl). The filtrate from the second crystallisation was set aside at room temperature. A small crop of crystals (220 mg, ratio 20:80, meso:dl) was removed and then the filtrate concentrated in vacuo giving dl-enriched material (1.41 g, ratio 22:78, meso:dl). Slow recrystallisation from ethyl acetate gave pure dl isomer as large clear crystals (82 mg), m.p. 129°–130° C.

EXAMPLE 15

X-ray Crystallography

Crystal suitable for X-ray crystallography were obtained by crystallisation of the separated diastereoisomers from methanol. Details of the structure determination are given below. The determinations demonstrate that the diastereoisomer with an HPLC retention time of 8.90 minutes (Example 14.A) is the meso-diastereoisomer, while the diastereoisomer with a retention time of 9.87 minutes is the dl-diastereoisomer. In both cases, the configuration of the oxime functionalities is EE.

(a) Meso isomer $C_{13}H_{28}N_4O_2 \cdot \frac{1}{2}H_2O$, M=281, orthorhombic, space group $P2_12_12$, a=16.946, b=15.565, c=6.318. Å, V=1666.46 Å$^3$, Z=4, $D_c$=1.119 gcm$^{-3}$, F(000)=618, μ(Mo-Kx)=0.47 cm$^{-1}$. 1716 intensities were recorded (3<θ<25°) on a Philips PW1100 diffractometer. R 0.064 for 1036 reflections with F>6αF.

(b) dl isomer $C_{13}H_{28}N_4O_2$, M=272, monoclinic, space group C2/C, a=6.763, b=10.92, c=23.863 Å, V=1600.79 Å$^3$, Z=4, $D_c$=1.128 gcm$^{-3}$, F(000)=600, (Mo-K)=0.49 cm$^{-1}$. 1448 intensities were recorded (3<θ<25°) on a Philips PW1100 diffractometer. R 0.071 for 861 reflections with F>6αF.

EXAMPLE 16

The $^1$H and $^{13}$C NMR Spectra of the meso- and d,l-diastereoisomers of Compound 1

1. $^1$H NMR Spectra $^1$H NMR spectra were run in d$_6$-DMSO at 500 MHz using a Bruker AM-500 FT NMR spectrometer. The following assignments were made. (For the carbon atom numbering, see the diagram above entitled "Diastereoisomers of Compound 1"):

| Chemical Shift | Multiplicity | Assignment |
| --- | --- | --- |
| 0.7748 | s | $(CH_3)_2$—$C_6$ (meso-) |
| 0.7779 | s | |
| 0.7835 | s | $(CH_3)_2$—$C_6$ (d,l-) |
| 1.06905 | d, J = 6.73 | $CH_3$—$C_3$ + $CH_3$—$C_9$ (d,l-) |
| 1.0660 | d, J = 6.74 | $CH_3$—$C_3$ + $CH_3$—$C_9$ (meso-) |
| 1.6437 | s | $CH_3$—$C_2$ + $CH_3$—$C_{10}$ |
| 2.1112 | d of AB q's | H's at $C_5$ + $C_7$ |
| 3.1235 | ABq,br | H's at $C_3$ + $C_9$ |
| 3.30 | s,br | NH's |
| 10.2495 | s | Oxime OH's |
| 10.2511 | s | |

In the d,l-diastereoisomer, the methyl groups attached to $C_6$ are in equivalent environments, and so should give a single signal. This has been assigned to the singlet at 0.7835 ppm. In the meso-diastereoisomer, the methyl groups attached to $C_6$ are in different environments, and so two singlets should be seen. These have been assigned to the singlets at 0.7748 and 0.7779 ppm.

2. $^{13}$C NMR Spectra $^{13}$C NMR spectra were run in d$_6$-DMSO or d$_4$-MeOH using a Bruker AM-250 FT NMR spectrometer or a Jeol FX-200 FT NMR spectrometer. The following assignments were made:

| Chemical shift/ppm | Assignment |
| --- | --- |
| 8.9485 | $CH_3$—$C_2$ + $CH_3$—$C_{10}$ |
| 19.3809 | $CH_3$—$C_3$ + $CH_3$—$C_9$ (meso-) |
| 19.4037 | $CH_3$—$C_3$ + $CH_3$—$C_9$ (d,l-) |
| 25.0265 | } $CH_3$—$C_6$ (meso-) |
| 25.0421 | |
| 25.0794 | $CH_3$—$C_6$ (d,l-) |
| 35.3182 | $C_6$ (d,l-) |
| 35.3731 | $C_6$ (meso-) |

-continued

| Chemical shift/ppm | Assignment |
| --- | --- |
| 57.8070 | $C_5$ + $C_7$ (meso-) |
| 58.3569 | $C_5$ + $C_7$ (d,l-) |
| 58.9974 | $C_3$ + $C_9$ (meso-) |
| 59.0111 | $C_3$ + $C_9$ (d,l-) |
| 161.3406 | $C_2$ + $C_{10}$ (d,l-) |
| 161.4497 | $C_2$ + $C_{10}$ (meso-) |

The assignments were supported by off-resonance and selective proton decoupling experiments.

As with the proton spectrum, the signals for the gem-dimethyl groups at $C_6$ are distinct for the two isomers. The clearest distinction between the isomers can be seen in the signals for the carbons $C_5$ and $C_7$, the signal for the d,l-diastereoisomer being seen approximately 0.55 ppm downfield of the corresponding signal for the meso-diastereoisomer. The relative integrations for these signals corresponded closely to the values obtained for the isomer ratios by HPLC for a wide variety of samples.

EXAMPLE 17

Separation of d- and l-enantiomers of Compound 1

The diastereoisomer of Compound 1 was treated with an equivalent of L-(+)-tartaric acid in hot ethanolic solution. The solution was allowed to cool, and the white solid was filtered off and recrystallised three times to give a (+)-tartrate salt of one enantiomer $[\alpha]_D^{25}$=28.08° (c=2.5, H$_2$O). M.p. 173°–175° C.

The filtrate from the above preparation was concentrated, and the salt was decomposed to give Compound 1 (of unknown enantiomer proportions) by dissolving in water, basifying to pH9, and filtering off the white solid. This was recrystallised from ethyl acetate to give white crystals. This sample was treated with an equivalent of D-(−)-tartaric acid in hot ethanolic solution, and the resulting white solid was recrystallised three times to give the (−)-tartrate of the other enantiomer, $[\alpha]_D^{25}$=27.67° (c=2.5, H$_2$O). M.pt. 167.5°–168° C.

The samples of the tartrate salts thus obtained were converted into the free bases by the method given above to give samples of d- and l-Compound 1. The (+)-tartrate salt gave l-Compound 1, $[\alpha]_D^{25}$= −2.52° (c=4, MeOH), and the (−)-tartrate salt gave d-Compound 1, $[\alpha]_D^{25}$= +2.51° (c=4, MeOH).

EXAMPLE 18

Separation of Compound 2 into its meso- and d,l Forms

The meso- and d,l-forms of Compound 2 were separated by HPLC using a modification of the HPLC conditions employed in Example 14. The only differences were that the solvent composition was 98% MeOH and 2% (0.4M) aqueous ammonia, instead of 85% and 15% respectively, and that the flow rate was 2 ml min$^{-1}$ with a preparative column. Under these conditions the faster-running isomer had a retention time of approximately 24 minutes, and that of the slower-running isomer was approximately 26 minutes. The isomers were separated by preparative HPLC, giving samples of approximately 90% purity as estimated by HPLC. From the $^1$H NMR spectra the diastereoisomer eluted first was designated meso-, and the fraction is the d,l-form.

EXAMPLE 19

Separation of the d,l and the meso-isomers of Compound 4

Partial separation of the d,l- and meso-isomers of Compound 4 was achieved using HPLC with the same conditions as were used for Compound 2. The results indicated that although the isomer separation was poor, samples of ~70%:30% proportions were obtained. As oxime isomerism occurred very rapidly, it was not possible to isolate samples of greater purity.

EXAMPLE 20

Separation and Labelling of Oxime Isomers of Compound 1

Due to rapid equilibration effects, the (E,Z)-oxime isomer of Compound 1 had proved impossible to characterize as an isolated component. However, the labelling of the (E,Z) oxime isomer was studied, by isolation of the HPLC peak corresponding to the (E,Z) oxime isomer with immediate labelling of the resulting solution. Experiments using the (E,E) isomer showed that labelling under these conditions proceeded smoothly. Using the (E,Z)-isomer it was not possible to obtain consistent results, due in part to irreproducibility of the HPLC method and in part to the equilibration process; however, a number of complexes were obtained, including a lipophilic species (usually ~20%, and probably derived from the (E,E)-isomer from re-equilibration of the (E,Z)-isomer) and several more hydrophilic species.

EXAMPLE 21

Formation of the Tc-99m Complex of Compound 1

A sterile freeze dried formulation of 1.0 mg of the compound 1 (a dl/meso mixture) and 15 mg of stannous tartrate in a sealed 10 ml glass vial containing a nitrogen atmosphere, was reconstituted with 3–8 ml of eluate of Tc-99m pertechnetate, obtained from a Mo-99/Tc-99m generator system. Analysis of the resultant mixture indicated that reduction of pertechnetate (to a lower oxidation form of technetium), and complexation of the reduced technetium by the ligand is complete after standing at ambient temperatures for 1 minute.

The Tc-99m complexes of Compounds 2 to 13 and individual isomers and enantiomers thereof were formed similarly.

An alternative and currently preferred formulation consists of 0.5 mg of compound 1 (dl-isomer), 4.5 mg of sodium chloride, and 7.6 mg of stannous chloride dihydrate.

Analysis of the Tc-99m complexes

Thin Layer Chromatography

Glass fibre strips impregnated with silica gel form the stationary phase of a fast and accurate analytical system. Two strips, each measuring 20 cm×2 cm were used in each analysis. Approximately five microliters of the solution containing the complex was applied 1 cm from the base of each strip, and one strip developed with saline, the other with methylethylketone (MEK).

Determination of the distribution of radioactivity along each strip was conducted by means of a 100 channel analysis system interfaced to a Nova computer, programmed for peak integration. The Table below indicates the RF values of the major components of the Tc-99m solutions. The observed radiochemical purity of the Tc-99m complexes was generally greater than 80%.

| Silica gel on glass fibre chromatography | | |
|---|---|---|
| | Observed RF values | |
| Eluent: | MEK | Saline |
| Tc-99m colloid | 0 | 0 |
| Tc-99m pertechnetate | 1.0 | 1.0 |
| Tc-99m complexes | 0.9–1.0 | 0.0–0.2 |

Stability of the complexes

Radiochemical purity determinations by thin layer chromatography were carried out at several time points following formation of the technetium complexes of compounds 1 and 2 (a dl/meso mixture in each case) to determine the stability of the complexes. Typical results are shown in the table below.

| | % of the desired Tc-99m complex Time post formation | | |
|---|---|---|---|
| Tc-99 m complex of: | 2 min | 60 min | 120 min |
| Compound 1 | 92 | 87 | 79 |
| Compound 2 | 82 | 60 | 47 |

The in vitro stability of the complex of compound 2 is seen to be greatly inferior to that of the complex of compound 1. These differences are important. The percent of the Tc-99m not in the form of the complex is at all times more than twice as great with Compound 2 as with Compound 1. This radiochemical impurity would increase the background radiation in vivo to a point at which useful information would be more difficult or even impossible to obtain.

EXAMPLE 22

Animal biodistribution data 0.1 ml of the Tc-99m complex solution was administered by intravenous injection (lateral tail vein) to each of five or six rats (140–220 g). The injected dose was equivalent to approximately 1 mCi of Tc-99m. Three rats were sacrificed at 2 minutes post injection, and 3 at 1 hour or 2 at 2 hours post injection. At dissection, the organs and blood samples shown in the following table were taken, and assayed for radioactivity. The uptake in each organ or tissue was calculated as a percentage of the total activity recovered.

The ratio of diastereoisomers in the Tc-99m complexes used in this experiment is not known.

| Biodistribution data of Tc-99m complexes of ligands (no separation of stereoisomers) | | | | | | | | |
|---|---|---|---|---|---|---|---|---|
| Tc-99m Complex of ligand | % id/organ in rats | | | | | | | |
| | 2 min pi | | | | 1 or 2 hr pi | | | |
| | Brain | Heart | Liver | Blood | Brain | Heart | Liver | Blood |
| 1 | 1.5 | 0.4 | 8.4 | 16.7 | 1.2 | 0.2 | 5.4 | 19.6 (1 hr) |

| Biodistribution data of Tc-99m complexes of ligands (no separation of stereoisomers) | | | | | | | | |
|---|---|---|---|---|---|---|---|---|
| Tc-99m Complex of ligand | % id/organ in rats | | | | | | | |
| | 2 min pi | | | | 1 or 2 hr pi | | | |
| | Brain | Heart | Liver | Blood | Brain | Heart | Liver | Blood |
| 2 | 1.6 | 0.5 | 10.9 | 14.6 | 1.4 | 0.5 | 4.9 | 12.4 (1 hr) |
| 3 | 1.1 | 0.2 | 27.8 | 6.8 | 0.7 | 0.1 | 17.0 | 2.1 (2 hr) |
| 4 | 1.6 | — | 15.6 | 13.4 | 1.5 | — | 12.7 | 5.7 (1 hr) |
| 5 | 0.8 | — | 18.0 | 10.5 | 0.6 | — | 12.1 | 2.8 (1 hr) |
| 6 | 1.2 | 0.4 | 19.6 | 5.8 | 0.4 | 0.2 | 13.5 | 2.6 (2 hr) |
| 7 | 1.0 | — | 20.6 | 7.4 | 0.5 | — | 36.5 | 3.3 (1 hr) |
| 10 | 0.4 | 0.5 | 32.9 | 14.0 | 0.6 | 0.3 | 16.9 | 2.7 (2 hr) |
| 11 | 1.3 | 0.8 | 12.3 | 11.9 | 1.0 | 0.4 | 10.2 | 4.7 (1 hr) |
| 12 | 1.0 | 0.5 | 23.9 | 8.6 | 0.9 | 0.3 | 19.7 | 6.0 (1 hr) |
| 13 | 0.5 | 0.6 | 15.9 | 15.2 | 0.2 | 0.2 | 12.5 | 7.2 (1 hr) |

The results at 2 minutes and 1 hour p.i. are the mean of 3 animals.
The results at 2 hours p.i. are the mean of 2 animals.

EXAMPLE 23

The experiment of Example 22 was repeated using the separated diastereoisomers of compound 1. The results are given in the Table below and should be compared to those for compound 1 (the mixture) in the Table in Example 15.

| Biodistribution data on the Tc-99m complexes from d,l- and meso-diastereoisomers of compound 1. | | | | | | |
|---|---|---|---|---|---|---|
| Tc-99m complexes of | % id/organ in rats | | | | | |
| | 2 min p.i. | | | 1 hour p.i. | | |
| | Brain | Liver | Blood | Brain | Liver | Blood |
| d.1 | 1.99 | 9.42 | 11.42 | 1.90 | 9.25 | 10.17 |
| meso- | 0.78 | 26.86 | 5.33 | 0.53 | 24.24 | 3.17 |

The reasons for the differences in brain uptake and retention are not understood, but do not appear to result from any difference in lipophilicity between the Tc-99m complexes of the two isomers. We have compared the lipophilicities of the two complexes, by a special HPLC method developed by ourselves for this purpose, and have concluded that they are indistinguishable.

EXAMPLE 24

Rat Biodistribution Data on the Tc-99m Complexes From Isolated Stereoisomers (a) dl and meso diastereoisomers

| Compound No. | Stereo Isomer | % id/organ in rats | | | | | | | |
|---|---|---|---|---|---|---|---|---|---|
| | | 2 mins pi | | | | 1 hr pi | | | |
| | | Brain | Heart | Liver | Blood | Brain | Heart | Liver | Blood |
| 1 | meso | 1.1 | 0.6 | 19.9 | 5.0 | 0.7 | 0.2 | 23.7 | 3.1 |
| | dl | 2.1 | 1.2 | 11.3 | 11.0 | 1.6 | 0.7 | 11.9 | 8.6 |
| 2 | meso | 1.7 | 0.6 | 17.9 | 6.9 | 1.4 | 0.2 | 20.7 | 2.8 |
| | dl | 1.8 | 1.1 | 11.6 | 10.5 | 1.5 | 0.7 | 9.4 | 7.8 |

(b) d and l enantiomers of Compound 1

| Enantiomer | % id/organ in rats | | | | | |
|---|---|---|---|---|---|---|
| | 2 min pi | | | 1 hr pi | | |
| | Brain | Liver | Blood | Brain | Liver | Blood |
| d | 1.6 | 13.4 | 11.4 | 1.4 | 9.7 | 10.2 |
| l | 2.6 | 9.6 | 11.0 | 2.2 | 7.7 | 11.1 |

Data in Tables (a) and (b) are the mean from 3 animals at each time point. They were obtained at a different time and using different formulations from the data in Example 23.

EXAMPLE 25

Clinical Studies

All clinical studies, involving comparisons between the Tc-99m complexes of dl and meso, and d,l and dl stereoisomers of Compound 1 were conducted in normal volunteer subjects at Aberdeen Royal Infirmary.

(a) Comparison of dl and meso diastereoisomers of Compound 1

This study was published:

99mTc HM-PAO Stereoisomers as Potential Agents for Imaging Regional Cerebral Blood Flow—Human Volunteer Studies. Sharp P. F., Smith F. W., Gemmell H. G. et al. *J. Nucl. Med.*, 1986, 27, pages 171–177.

The following table demonstrates the mean percentage of total activity injected per organ at 20 minutes p.i. Data is then taken from area of interest studies employing a whole body scanning device.

| Tc-99m complex of Stereoisomer of Compound 1 | % injected activity | | | |
|---|---|---|---|---|
| | Brain | Liver | Kidneys | Bladder + Urine |
| meso | 1.85 | 16.6 | 1.3 | 0.6 |
| dl | 4.22 | 10.22 | 3.50 | 2.28 |
| Mixture | 1.95 | 13.0 | 1.95 | 1.4 |

(b) Comparison of d,l and dl stereoisomers of Compound 1

The following table gives the mean of three studies for each stereoisomer, of percentage of injected dose in normal volunteers at 30 minutes p.i.

| | Brain | Liver | Kidney |
|---|---|---|---|
| d | 3.76 | 12.66 | 1.46 |
| l | 4.30 | 8.06 | 4.0 |

| | Brain | Liver | Kidney |
|---|---|---|---|
| dl | 4.16 | 10.73 | 3.03 |

Clinical studies in normal volunteer subjects

The following data allows comparison of the relative performance of the complexes of compounds 1 and 2 (an unseparated dl/meso mixture in each case) in human volunteer subjects.

(i) Blood clearance

| Time post injection (minutes) | % id in blood | |
|---|---|---|
| | Compound 1 | Compound 2 |
| 14 | 9.54 | 11.06 |
| 40 | 7.73 | 6.9 |
| 60 | 6.38 | 5.93 |
| 250 | 5.26 | 3.98 |

(ii) Whole body distribution

| | Whole body distribution at 2 hrs p.i. | |
|---|---|---|
| | Compound 1 | Compound 2 |
| Brain | 3.70 | 3.48 |
| Liver | 23.35 | 13.21 |
| Bladder | 3.9 | 21.02 |

Tomographic Imaging Studies in man

Tomographic images of the brain were determined using the same complexes in normal volunteers. The device used was a single head rotating gamma camera and minicomputer system. 64 25-second images were accumulated by the gamma camera during 360° circular rotation of the head and shoulders of the volunteer.

Good quality tomographic images of the brain were obtained by the reconstruction of the images obtained using the complex of Compound 1 by the minicomputer. The images obtained using the complex of Compound 2 were less good, due to a higher level of background radiation, resulting from a higher uptake in soft tissue regions.

EXAMPLE 27

In vitro labelling of leucocytes

A solution of the technetium-99m complex of compound 1 was made as follows. A vial contained 0.5 mg compound 1; 7.5 mg stannous chloride dihydrate; and 4.5 mg sodium chloride; freeze-dried and sealed under nitrogen. To this was added 5.0 ml of sodium pertechnetate eluate from a 135mCi technetium generator.

Mixed leucocytes were obtained from 34 ml of acid citrate anticoagulated blood by dextran sedimentation. These were washed twice and resuspended in 2.0 ml phosphate buffered saline containing approximately 0.25 mg/ml prostaglandin El. The suspension was incubated with 0.2 ml of the solution of the technetium-99m complex of compound 1. Incubation was at ambient temperature, and samples were removed at intervals for analysis. After two minutes, 60% of the radioactivity was associated with blood cells; after 5 minutes, 83% and after 10 minutes, 89%.

Tc-99m labelled leucocytes prepared by this method were injected into rats bearing abscesses produced by implantation of sponge impregnated with faecal extract. Abscess uptake was identical to that for In-111 labelled leucocytes.

We claim:

1. A lipophilic macrocyclic complex, useful as a diagnostic radiopharmaceutical, of technetium-99m with a propylene amine oxime ligand having the formula:

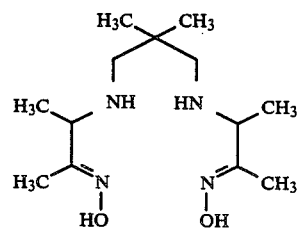

said complex being in the form of a single stereoisomer or a mixture of stereoisomers.

2. The complex according to claim 1 wherein the ligand is the dl-diastereoisomer.

3. The complex according to claim 1 wherein the ligand is the l-enantiomer.

4. The complex according to claim 1 wherein the ligand is the d-enantiomer.

5. A propylene amine oxime ligand having the formula:

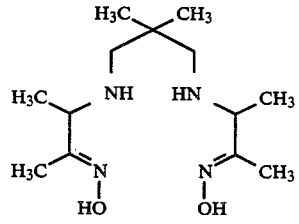

said ligand being in the form of a single stereoisomer or a mixture of stereoisomers.

6. The ligand according to claim 5 which is the dl-diastereoisomer.

7. The ligand according to claim 5 which is the l-enantiomer.

8. The ligand as claimed in claim 5 which is the d-enantiomer.

9. The complex according to claim 1, having the formula:

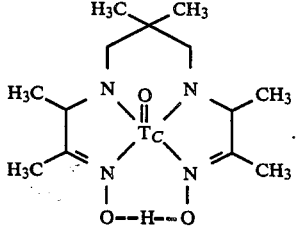

* * * * *